United States Patent [19]

Ryan

[11] Patent Number: 4,702,914

[45] Date of Patent: Oct. 27, 1987

[54] VETERINARY-SAUCE PROPHYLACTIC

[76] Inventor: Hillary A. Ryan, Box 934, Far Hills, N.J. 07931

[21] Appl. No.: 605,194

[22] Filed: Apr. 30, 1984

[51] Int. Cl.$^4$ ............... A61K 35/78; A61K 31/70; A61K 31/495; A23K 1/00
[52] U.S. Cl. ................... 424/195.1; 514/23; 514/255; 426/635; 426/805
[58] Field of Search ............... 424/195, 195.1; 426/635, 805; 514/23, 255

[56] References Cited

U.S. PATENT DOCUMENTS 4,247,562  1/1981  Bernotavicz ............... 426/72

*Primary Examiner*—J. R. Brown
*Assistant Examiner*—John W. Rollins, Jr.
*Attorney, Agent, or Firm*—William T. Hough

[57] ABSTRACT

In a preferred embodiment there is provided for application to ordinary pet food for dogs, cats, puppies and kittens, a dietary ketchup sauce inclusive of garlic as a prophylactic against flea infestation and of diethyl-carbamazine as a prophylactic against mosquito heartworm, and further inclusive of vitamins and minerals of dietary nature, dietary seed, salt, and honey.

12 Claims, No Drawings

VETERINARY-SAUCE PROPHYLACTIC

This invention is directed to a pet food sauce for improving both the enjoyment and acceptance of pet food by the pet while achieving various benefits of deterents against health hazards together with improved positive health nutritional benefits, for use on or with conventional pet foods typically for dogs, cats, puppies and kittens.

BACKGROUND TO THE INVENTION

While every pet owner has faced the problem of the dog or cat refusing or at-least being disinclined to eat various commercially available pet foods, little has been done to improve the nature thereof to make it more appetizing to the pet. If we human beings were to taste some of the junk labeled pet-food, perhaps we could understand why the pets reject it. Moreover, it has been reasonably established by various researchers, that the commercial pet foods are often made from sub-standard meats and/or other sub-standard ingredients and too often are lacking in the desired and needed nutritional ingredients for the good health of our pets. Equally as important, however, unfortunately too frequently too late we learn of or discover the existence of environmental health hazards requiring often expensive advance preventative medications and/or treatments to avoid sickness and even possible the early untimely death of our cherished pets. Few pet owners are aware of the fact that proper nutritional care of the pet can ward-off some of such hazards. Whilenot all-inclusive, two more prominent such typical health hazards of an environmental nature are fleas and mosquitoes, together with the various health-associated problems and diseases associated with each. As equally important, if our pets become diseased, they are often also immediate health hazards to us or to our children. While because of the notorious nature of fleas little need be said of the importance of preventing fleas infestation of our pets, less is known often, or the actual severity of the threat and recognition that death of the pet can easily result quickly, with regard to the mosquto-transmitted heart-worm that can and often does cause pet deaths shortly after the pet is bit by a carrier-mosquito. And many mosquitoes do in fact carry this hazard to the pet, which if bitten may quickly develop a lethal heart worm. On the other hand, few pet owners take the time to have their pet immunized against such threat as that of heart worm. And as to fleas, too frequently owners rely on flea-collars or the like, the fumes of which are of questionable benefits if one considers that the pet is likewise constantly breathing those fumes that chase-off the fleas.

OBJECTS OF THE INVENTION

Objects of the present invention include the preventing or avoiding of one or more problems discussed above, together with obtaining improved health and happiness of family pets, by providing a food-supplementing sauce utilizable on or with other food fed to the pet(s).

Another object is to include in a pet food sauce particular predetermined prophylactic ingredients, and/or nutritional ingredients for use on or with other food fed to the pet(s), to assist in improved pet health and warding-off of detrimental diseases or health hazards.

A more particular object is to obtain a pet-ketchup sauce that improves the taste of and acceptance of conventional pet-foods while achieving one or more of above-noted other objects of the invention.

BROAD DESCRIPTION OF THE INVENTION

While other objects become apparent from the following disclosure, and the obtaining thereof apparent, the invention may be broadly described as a pet or veterinary food sauce that includes as essential basic ingredients a predominant or major amount of conventional ketchup sauce, and having substantially homogeneously distributed therethrough a minor therapeutic amount of a veterinary composition of prophylactic nature against some parasitic infestation. Typical of parasites causing health hazards, as above-noted, are fleas, but also ticks, and mosquitoes together with the heart-worm that results in the pet following the bite of the pet by the mosquito. Accordingly, a pet or veterinary prophylactic food or composition includes one or more ingredients used in the treatment and/or prevention thereof. The conventional ketchup sauce obviously includes a tomatoe-base in sauce form typically seasoned with vinegar, sugar and spices; however, for the present invention, vinegar is not essential but perhaps may be included, depending upon the variation desired as governed by the particular pet-type and its acceptance or rejection of a vinegar-containing ingredient; however, any suitable sweetner may be utilized either of sugar or synthetic type. Likewise, any of various spices and/or flavors or flavoring ingredients may be included, either natural or synthetic, not necessrily a "spice" in name. Additionally, other desired ingredients may be included.

Preferably as a sweetening agent, a honey of one or more varieties is utilized, such being of recognized beneficial food or nutritional content.

While the benefit of garlic or yeast content in a food has been recognized for pets as a deterent against fleas, there has not heretofore been any use thereof on a commercial basis, nor in anything in the nature of a food-supplementing sauce such as ketchup. Accordingly, while other natural or synthetic food ingridient(s) that are presently recognized as propylactic or preventative medication against flea and/or tick and/or other insect infestation, may be used as an inventive embodiment; accordingly, garlic may be included in minor amount within the ketchup sauce as a part thereof, as a typical prophylactic of the ketchus sauce of this invention, for application to or mixed with other dog, puppy, cat or kitten food at the time of feeding the pet(s).

Additionally, as with human beings, zinc is a dietary element that is desirable and important to the maintaining of healthy skin and other benefits, and likewise vitamin E, these being of particular importance in the preventing of aging from the lack of good circulation facilitated by capillary growth induced by vitamin E. These, either or both, alone or together with other important vitamins such as A, $D_2$, iron,potassium,-niacinamide, $B_{12}$, and the like, are also preferably included substantially homogeneously dispersed throughout the ketchup sauce of this invention.

Other typical ingredients of the ketchup sauce of the invention, include one or more of clove, cinnamon, celery or other dietary nutritionally beneficial seed(s), red pepper, salt of either or both sodium and/or potassium varieties.

A preferred prophylactic ingredient alone or together with other prophylactic ingredient(s), is the antiheart-worm medication(s) of which a well-known one is diethyl-carbamazine, which as an oral medication may be and preferably is included as a prophylactic ingredient of the ketchup food sauce of this invention.

While most prophylactic medication-type agents for oral administration, are stable against deterioration when admixed with other water-containing foods or ingredients, such as the watercontaining ketchup of theppresent invention, for any such prophylactic agent or composition that does not have long-term stability when admixed with particular food ingredients as the present ketchup sauce, it is within the scope of the present invention to include with the package a separately-packaged prophylactic ingredient which is admixed at the time of application of the ketchup sauce of this invention to the pet-food being served to the pet.

DETAILED DESCRIPTION

While the forms in which most vitamins and/or minerals is well known, such being conventionally and commercially available as dietary supplement sold often separately on the mark place, and many thereof being conventional ingredients of breakfast cerials of we human beings, with such cerial boxes itemizing the exact chemical compositions, typical compositions are as follow.

As is well known, there are various types of honey, such as for example, wheat honey, or fruit honey—of various fruit crops, or clover-type honey. Each of these honey compositions have their own different distinctive tastes. In any event, most animals and/or pets love and cherish the taste of honey, and additionally the use of honey in the place of sugar is much more healthful and nutritional for the animal. Not only does honey have nutritionaly benefits, as stated by many authorities, not fully known as to the exact ingredients thereof, but additionally the use of white sugar is associated with or at least widely speculated to be a causative factor in many health problems separate and apart from mere fat, such not being associated with the lactos-sugar of honey, which is equivalent to partially digested sugar. Accordingly, for each and all of these reasons, honey is a preferred sugar-type ingredient of the present ketchup sauce.

Minced or serrageted or chopped or powdered garlic, and/or yeast, each is commercially available, each a basic minor preferred ingredient of the present ketchup sauce, as typical prophylactic deterent against fleas,-,mosquitoes, ticks and the like, for pets that have such as a part of pet-food diet.

Zinc is commercially available in various oral forms, a particular one being zinc gluconate—a zin-sugar. Such, in particulate or powdered form is included in the ketchup sauce of the present invention, for improved skin conditioning and hair conditioning of the pets, whose coats are constantly subjected to heat-drying and soiling and other detrimental environmental conditions and adversities. Inclusion of a daily minor amount of such ingredient, as with food supplementing ketchup sauce of this invention, enhances skin condition as recognized conventionally but heretofore neglected in so far as the care of our pets.

A typical vitamin $B_{12}$ ingredient is cobatamine concentrate.

Iron may be in any of various conventionally recognized and/or commercial forms, but preferably is in the form of a particulate or powdered liver extract, distributed throughout the ketchup sauce of this invention.

Salt most conventionally is in the form of sodium chloride, but preferably also includes potassium chloride, potassium being another mineral often substantially overlooked as a conscious need for animals even though such is well known as essential in diets for humans in electrolyte balance of the blood, and for good heart rhythym—such being particularly important for an aging pet.

Vitamin E is often used in human beings having severe skin burns where excessive capillary growth is essential and desired. Likewise, vitamin E has been recognized as important for capillary development to assure continued adequate blood supply to the heart and to the brain, particularly during the aging years of human beings. Likewise, pets which age much faster than we human beings, benefit from improved circulation, including the blood supply to the skin and hair or fur-coating of the pet. Vitamin E may be in any of the commercially available forms, preferably in a particulate form, but may be in liquid form, distributed or for distribution throughout the ketchup sauce to be applied to the conventional pet food.

It is to be recognized that the present inventive ketchup sauce for pets may also be served alone, as a food, but preferably is applied to other liquid or solid pet food. It is also possible and within the scope of the invention, to admix with other food ingredients prior to packaging the other food.

However, the present invention has asaa novel and preferred feature thereof, its availability separate and apart from the conventional foods, as a supplement for application thereto to improve the acceptance of the food to and by the pet, together with the multiple concurrent benefits of the present ketchup sauce above-inumerated.

It is within the scope of the invention to make such variations and substitution of equivalents as would be apparent to a person of ordinary skill in this particular art.

Accordingly, the various ingredients may be admixed by any conventional or desired way, and placed in a container for storage and sale. The ingredients may also include any one or more of conventional preservative chemical additives currently available on the market, or as desired, for food stuffs.

Application to food may be from a bottle, can, or plastic squeeze container, for example, onto the food, onto the surface of the food, or may be admixed with the food as might be desired.

No relevant patents are known. A sole patent of interest located in a novelty patent search, is Bernotaviez U.S. Pat. No. 4,247,562 issued Jan. 27, 1981, as a chunk-food product inclusive of gravy. Merely one of several embodiments showing a minor amount of tomato paste, relative to major amount of beef gravy mix and other ingredients such as vitamins and minerals, wheat flour, etc.

I claim:

1. A veterinary food sauce comprising in combination: a ketchup sauce; and a minor amount of a veterinary prophylactic composition, relative to amount of said ketchup sauce.

2. A veterinary food sauce of claim 1, including a minor amount of a dietary mineral, relative to said amount of said ketchup sauce.

3. A veterinary food sauce of claim 2, including a minor amount of a dietary vitamin composition, relative to said amount of said ketchup sauce.

4. A veterinary food sauce of claim 3, in which said prophylactic composition includes diethyl-carbamazine.

5. A veterinary food sauce of claim 1, in which said prophylactic composition includes diethyl-carbamazine.

6. A veterinary food sauce of claim 1, including a minor amount of dietary vitamin composition, relative to said amount of said ketchup sauce.

7. A veterinary food sauce of claim 6, in which said vitamin composition includes a plurality of vitamins.

8. A veterinary food sauce of claim 1, in which said ketchup sauce comprises tomato in sauce form, dietary seed, salt, and a sugar composition.

9. A veterinary food sauce of claim 8, in which said sugar composition includes a major amount of honey, relative to any other of said sugar composition.

10. A veterinary food sauce of claim 9, including a minor amount of each of dietary minerals and dietary vitamins relative to said amount of said ketchup sauce, and in which said prophylactic composition includes diethyl-carbamazine in a therapeutic amount sufficient to ward-off pet parasites from a pet that consumes the food sauce.

11. A veterinary food sauce of claim 10, including a minor amount of garlic, relative to said amount of said ketchup sauce.

12. A veterinary food sauce of claim 1, including a dietary prophylactic that is effective against flea infestation of a pet that consumes the food sauce.

* * * * *